(12) United States Patent
Lu et al.

(10) Patent No.: US 10,588,978 B2
(45) Date of Patent: Mar. 17, 2020

(54) PHARMACEUTICAL COMPOSITION CONTAINING IMIDAZOLINE DERIVATIVE

(71) Applicant: Jiangsu Hengrui Medicine Co., Ltd., Lianyungang, Jiangsu (CN)

(72) Inventors: Yun Lu, Jiangsu (CN); Xinhua Zhang, Jiangsu (CN); Daimei Zhang, Jiangsu (CN)

(73) Assignee: JIANGSU HENGRUI MEDICINE CO., LTD., Lianyungang, Jiangsu (CN)

(*) Notice: Subject to any disclaimer, the term of this patent is extended or adjusted under 35 U.S.C. 154(b) by 0 days.

(21) Appl. No.: 16/077,610

(22) PCT Filed: Feb. 17, 2017

(86) PCT No.: PCT/CN2017/073868
§ 371 (c)(1),
(2) Date: Aug. 13, 2018

(87) PCT Pub. No.: WO2017/140253
PCT Pub. Date: Aug. 24, 2017

(65) Prior Publication Data
US 2019/0038755 A1    Feb. 7, 2019

(30) Foreign Application Priority Data

Feb. 19, 2016    (CN) .......................... 2016 1 0093969

(51) Int. Cl.
| | |
|---|---|
| A61K 47/38 | (2006.01) |
| A61K 47/26 | (2006.01) |
| A61K 47/12 | (2006.01) |
| A61K 31/4166 | (2006.01) |
| A61K 9/20 | (2006.01) |
| A61K 9/16 | (2006.01) |
| A61P 35/00 | (2006.01) |
| A61J 3/07 | (2006.01) |

(52) U.S. Cl.
CPC ................. *A61K 47/38* (2013.01); *A61J 3/07* (2013.01); *A61K 9/1652* (2013.01); *A61K 9/2018* (2013.01); *A61K 9/2054* (2013.01); *A61K 9/2095* (2013.01); *A61K 31/4166* (2013.01); *A61K 47/12* (2013.01); *A61K 47/26* (2013.01); *A61P 35/00* (2018.01)

(58) Field of Classification Search
None
See application file for complete search history.

(56) References Cited

FOREIGN PATENT DOCUMENTS

| | | |
|---|---|---|
| CN | 103958480 A | 7/2014 |
| WO | 2014036897 A1 | 3/2014 |

OTHER PUBLICATIONS

Scardino. The prevention of prostate cancer—the dilemma continues. N. Engl. J. Med. 349;3. Jul. 17, 2003.*
Int'l Search Report dated May 19, 2017 in Int'l Application No. PCT/CN2017/073868.
The second method (paddle method) of the dissolution rate test disclosed in the appendix of vol. IV of Chinese Pharmacopeia (2015 Edition).
Zhang et al, "Development of Novel Anticancer Drugs," Chinese Journal of New Drugs, vol. 19, No. 24, pp. 2277-2284 and p. 2289 (Dec. 2010).

* cited by examiner

*Primary Examiner* — Anna Pagonakis
(74) *Attorney, Agent, or Firm* — Panitch Schwarze Belisario & Nadel LLP

(57) ABSTRACT

Provided in the present invention is a pharmaceutical composition containing an imidazoline derivative. In particular, the pharmaceutical composition provided in the present invention contains (S)-4-(3-(4-(2,3-dihydroxypropoxy)phenyl)-4,4-dimethyl-5-carbonyl-2-thioxoimidazolidin-1-yl)-2-(trifluoromethyl)benzonitrile and cellulose ether; and the composition has a good stability, dissolution rate and bioavailability.

19 Claims, No Drawings

PHARMACEUTICAL COMPOSITION CONTAINING IMIDAZOLINE DERIVATIVE

CROSS-REFERENCE TO RELATED APPLICATION

This application is a Section 371 of International Application No. PCT/CN2017/073868, filed Feb. 17, 2017, which was published in the Chinese language on Aug. 24, 2017, under International Publication No. WO 2017/140253 A1, which claims priority under 35 U.S.C. § 119(b) to Chinese Application No. 201610093969.7, filed Feb. 19, 2016, the disclosures of which are incorporated herein by reference in their entirety.

FIELD OF THE INVENTION

The present invention belongs to the field of pharmaceutical formulations. Specifically, the present invention relates to a pharmaceutical composition comprising (S)-4-(3-(4-(2,3-dihydroxypropoxy)phenyl)-4,4-dimethyl-5-carbonyl-2-thioimidazolin-1-yl)-2-(trifluoromethyl)benzonitrile.

BACKGROUND OF THE INVENTION

Prostate cancer (PCa) is a malignant tumor that occurs in the prostate tissue of males, and is the result of abnormal disordered growth of prostate acinar cells. The differentiation and growth of normal prostate epithelial cells as well as the development of prostate cancer all depend on androgen that is mainly (about 80-90%) synthesized in testis. Synthetic androgen binds to the androgen receptor (AR) after entering the cells, and causes the dissociation of heat shock protein (HSP) from the AR, then the AR enters the nucleus and activates multiple downstream genes, including prostate-specific antigen (PSA). Early prostate cancer is sensitive to androgen, orchiectomy (castration) thus can significantly inhibit the development of prostate cancer. However, the castration surgery is effective for a certain period of time, and many patients undergo the transformation from androgen-dependent to androgen-independent within a period of time after castration. The prostate cancer of these patients develops into the androgen independent prostate cancer (AIPC), and the anti-androgen therapy is no longer effective to them. The occurrence of AIPC still has an important relationship with the activation of AR signaling pathway in PCa cells.

The first-generation drugs, which aim at inhibiting AR activity, include Bicalutamide (or Casodex) and Flutamide. The second-generation AR antagonist drugs for AIPC therapy include MDV3100 and ARN-509. MDV3100 is the first second-generation non-steroidal AR antagonist drug in the world, and was approved by the FDA at the end of August 2012. The affinity of MDV-3100 to AR is 5-8 times higher than that of bicalutamide. MDV-3100 can inhibit the growth of AIPC in mouse and human by inhibiting AR activity, and has no effect of promoting tumor cell growth.

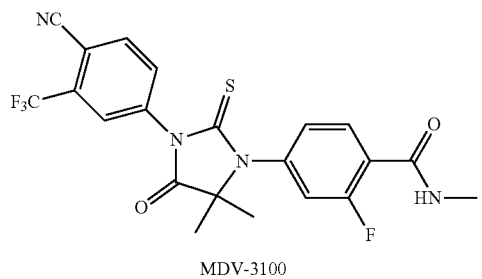

MDV-3100

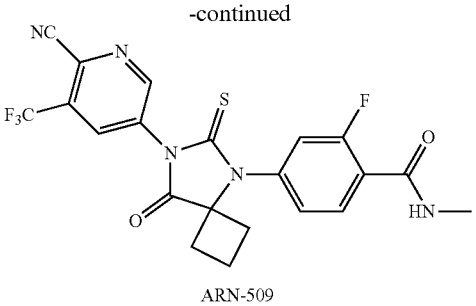

ARN-509

WO2014036897A1 discloses novel AR antagonists, including a compound of formula (I), with a chemical name of (S)-4-(3-(4-(2,3-dihydroxypropoxy)phenyl)-4,4-dimethyl-5-carbonyl-2-thioimidazolin-1-yl)-2-(trifluoromethyl)benzonitrile. The activity in vitro of this compound is slightly better than that of MDV-3100, and the hERG inhibition rate is further improved (IC50: 24.83 μM). The inhibition half lives of this compound on five major subtypes of CYP450 are all greater than 50 μM. The in vivo exposure of this compound in rats is comparable to that of MDV-3100, and the in vivo exposure of this compound in dogs is more than six times that of MDV-3100, at the same dose and in the same solvent. The compound of formula (I) has only one chiral center. The chiral starting material is easy to obtain, and the synthesis difficulty is greatly reduced. In addition, the compound of formula (I) has no AR agonist activity at 3 μM and 10 μM, and the ratio of the drug concentration in brain tissue to the drug concentration in plasma in mice is much lower than that of MDV-3100 compound, and so the possibility of epileptic side effects is smaller. Therefore, the compound of formula (I) has a broad clinical prospect.

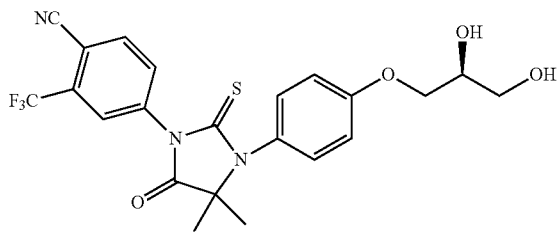

(I)

However, the above-mentioned document does not disclose how to obtain a stable pharmaceutical composition comprising the above-mentioned compound and the dissolution rate which meets the requirement. Studies have found that the above-mentioned compound has poor stability, and some conventional formulations cannot guarantee the stability of the composition; meanwhile, the compound is poorly soluble in a lot of compositions prepared with conventional auxiliaries. Therefore, in-depth studies are required to find a stable composition with a good dissolution rate.

SUMMARY OF THE INVENTION

The object of the present invention is to provide a pharmaceutical composition with good stability and rapid dissolution. The process for preparing the pharmaceutical composition is simple and is more suitable for large-scale production.

The pharmaceutical composition according to the present invention comprises an active ingredient and a cellulose ether, wherein the active ingredient is (S)-4-(3-(4-(2,3-dihydroxypropoxy)phenyl)-4,4-dimethyl-5-carbonyl-2-thioimidazolin-1-yl)-2-(trifluoromethyl)benzonitrile. The active ingredient is present in an amount of 5%-50%, and preferably 10%-25% by weight, relative to the total weight of the pharmaceutical composition.

The cellulose ether can be one or more selected from the group consisting of alkyl cellulose, hydroxyalkyl cellulose and hydroxyalkyl alkyl cellulose, preferably hydroxyalkyl cellulose. The hydroxyalkyl cellulose is one or more selected from the group consisting of hydroxyethyl cellulose and hydroxypropyl cellulose, preferably hydroxypropyl cellulose, and more preferably hydroxypropyl cellulose SSL and SL. The hydroxyalkyl alkyl cellulose is one or more selected from the group consisting of hydroxyethyl methyl cellulose and hydroxypropyl methyl cellulose.

The content of cellulose ether is not particularly limited. In a preferred embodiment, the cellulose ether is present in an amount of 0.5%-50%, preferably 0.5%-15%, and most preferably 0.5%-10% by weight, relative to the total weight of the pharmaceutical composition.

In a particularly preferred embodiment, the pharmaceutical composition of the present invention comprises hydroxypropyl cellulose, which can significantly improve the compatibility with the active ingredient, and improve the dissolution rate and bioavailability of the drug.

The pharmaceutical composition according to the present invention can comprise a filler, wherein the filler can be one or more selected from the group consisting of lactose, mannitol, microcrystalline cellulose and pregelatinized starch. The filler is present in an amount of 30%-95% by weight, relative to the total weight of the pharmaceutical composition. In an embodiment of the present invention, the fillers used are lactose and microcrystalline cellulose, and the total amount of the two is 40-80%, preferably 60-75%.

The pharmaceutical composition according to the present invention can comprise a disintegrant, wherein the disintegrant can be one or more selected from the group consisting of croscarmellose sodium, sodium carboxymethyl starch, low-substituted hydroxypropyl cellulose and crospovidone. The disintegrant is present in an amount of 3%-20% by weight, relative to the total weight of the pharmaceutical composition.

The pharmaceutical composition according to the present invention can comprise a lubricant, wherein the lubricant can be one or more selected from the group consisting of magnesium stearate, stearic acid, and glyceryl behenate. The lubricant is present in an amount of 0.1-2% by weight, relative to the total weight of the pharmaceutical composition.

In a most preferred embodiment, the present invention provides a pharmaceutical composition, comprising the following ingredients:

1) 5%-50% by weight of (S)-4-(3-(4-(2,3-dihydroxypropoxy)phenyl)-4,4-dimethyl-5-carbonyl-2-thioimidazolin-1-yl)-2-(trifluoromethyl)benzonitrile;

2) 0.5%-10% by weight of hydroxypropyl cellulose;

3) 40-80% by weight of a filler, wherein the filler is a mixture of lactose and microcrystalline cellulose;

4) 3%-20% by weight of a disintegrant, wherein the disintegrant is one or more selected from the group consisting of croscarmellose sodium and sodium carboxymethyl starch; and 5) 0.1-2% by weight of a lubricant, wherein the lubricant is one or more selected from the group consisting of magnesium stearate, stearic acid, and glyceryl behenate.

The pharmaceutical composition of the present invention can be prepared by methods commonly used in the art. For example, a method such as high shear wet granulation, dry granulation, and one step granulation is used to prepare the granules of the pharmaceutical composition, which are then compressed into tablets or filled into capsules.

Due to the presence of cellulose ether such as hydroxypropyl cellulose, the stability of the pharmaceutical composition according to the present invention has been improved. After testing, when the composition of the present invention is placed under a closed condition at 60° C. for 4 weeks, the increase of related substances does not exceed 0.3%, preferably 0.2%, more preferably 0.1%, and most preferably 0.05%.

On the other hand, the dissolution of the composition of the present invention is very complete. The dissolution test is carried out on the composition of the present invention according to the second method (paddle method) of the dissolution rate test described in the appendix of volume IV of Chinese Pharmacopoeia (2015 Edition), using a 0.5% aqueous solution of sodium dodecyl sulfate (SDS) (the volume is preferably 1000 ml) as a dissolution medium at 37±0.5° C. and at a paddle speed of 50 rpm. The dissolution rate is greater than or equal to 95% at 45 minutes or at 60 minutes.

DETAILED DESCRIPTION OF THE INVENTION

The present invention is further described in detail by the following examples and experimental examples. These examples and experimental examples are for illustrative purposes only, and are not intended to limit the scope of the present invention.

Examples 1 to 4

(S)-4-(3-(4-(2,3-dihydroxypropoxy)phenyl)-4,4-dimethyl-5-carbonyl-2-thioimidazolin-1-yl)-2-(trifluoromethyl)benzonitrile (hereinafter referred to as compound A), lactose or mannitol, microcrystalline cellulose, and croscarmellose sodium were weighed according to the ratio shown in Table 1, then wet granulation was carried out by a high speed shear granulator using a 5% aqueous solution of polyvinylpyrrolidone K30 as a binder. The wet and soft material was wet-milled and dried, then the dry granules (moisture content is less than 3%) were dry-milled. A prescription amount of magnesium stearate was added, and mixed well with the granules. The resulting total mixed granules were compressed into tablets.

TABLE 1

| | Examples (mg/tablet) | | | |
|---|---|---|---|---|
| Components | 1 | 2 | 3 | 4 |
| Compound A | 100 | 100 | 100 | 100 |
| Lactose | — | 270.0 | 310.0 | 230.0 |
| Mannitol | 270.0 | — | — | — |
| Microcrystalline cellulose | 85.0 | 85.0 | 45.0 | 125.0 |
| Croscarmellose sodium | 25.0 | 25.0 | 25.0 | 25.0 |
| Polyvinylpyrrolidone K30 | 12.8 | 11.7 | 9.7 | 13.1 |
| Magnesium stearate | 5.0 | 5.0 | 5.0 | 5.0 |
| Total | 498 | 497 | 495 | 498 |

Experimental Example 1: Dissolution Test

The dissolution rates of the tablets of Examples 1-4 were determined according to the second method (paddle method) of the dissolution rate test disclosed in the appendix of volume IV of Chinese Pharmacopeia (2015 Edition). The dissolution test was carried out using 1000 ml of 0.5% aqueous solution of sodium dodecyl sulfate (SDS) as a dissolution medium at 37±0.5° C. and at the paddle speed of 50 rpm. The results show that the dissolution of compound A in Examples 1-4 is complete. The dissolution results are shown in Table 2.

TABLE 2

| Time  | Dissolution rate (%) | | | |
|-------|-----------|-----------|-----------|-----------|
| (min) | Example 1 | Example 2 | Example 3 | Example 4 |
| 5     | 38.0      | 35.1      | 36.2      | 38.4      |
| 15    | 78.9      | 79.0      | 77.8      | 81.0      |
| 30    | 92.1      | 93.1      | 92.0      | 93.2      |
| 45    | 96.9      | 98.9      | 97.8      | 99.0      |
| 60    | 97.2      | 98.9      | 98.7      | 98.6      |

Examples 5 to 6

(S)-4-(3-(4-(2,3-dihydroxypropoxy)phenyl)-4,4-dimethyl-5-carbonyl-2-thioimidazolin-1-yl)-2-(trifluoromethyl)benzonitrile (hereinafter referred to as compound A), lactose, microcrystalline cellulose, and croscarmellose sodium were weighed according to the ratio shown in Table 3, then wet granulation was carried out by a high speed shear granulator using an aqueous solution of polyvinylpyrrolidone K30, an aqueous solution of pregelatinized starch and an aqueous solution of hydroxypropyl cellulose SSL respectively as a binder. The wet and soft material was wet-milled and dried, then the dry granules (moisture content is less than 3%) were dry-milled. A prescription amount of magnesium stearate was added, and mixed well with the granules. The resulting total mixed granules were compressed into tablets.

TABLE 3

| Components | Examples (mg/tablet) | | |
|---|---|---|---|
|  | 2 | 5 | 6 |
| Compound A | 100 | 100 | 100 |
| Lactose | 270.0 | 255.0 | 270.0 |
| Microcrystalline cellulose | 85.0 | 85.0 | 85.0 |
| Croscarmellose sodium | 25.0 | 25.0 | 25.0 |
| Polyvinylpyrrolidone K30 (5%) | 11.7 | — | — |
| Pregelatinized starch (10%) | — | 28.4 | — |
| Hydroxypropyl cellulose SSL (5%) | — | — | 10.2 |
| Magnesium stearate | 5.0 | 5.0 | 5.0 |
| Total | 497 | 498 | 495 |

Experimental Example 2: Dissolution Test

The dissolution rates of the tablets of Examples 2, 5 and 6 were determined according to the second method (paddle method) of the dissolution rate test disclosed in the appendix of volume IV of Chinese Pharmacopeia (2015 Edition). The dissolution test was carried out using 1000 ml of 0.5% aqueous solution of sodium dodecyl sulfate (SDS) as a dissolution medium at 37±0.5° C. and at the paddle speed of 50 rpm. The results show that the dissolution of compound A in Example 5 is not complete; and the dissolution of compound A in Example 6 is complete. The dissolution results are shown in Table 4.

TABLE 4

| Time  | Dissolution rate (%) | | |
|-------|-----------|-----------|-----------|
| (min) | Example 2 | Example 5 | Example 6 |
| 5     | 35.1      | 28.9      | 36.7      |
| 15    | 79.0      | 76.5      | 80.9      |
| 30    | 93.1      | 89.0      | 94.9      |
| 45    | 98.9      | 90.1      | 99.8      |
| 60    | 98.9      | 92.7      | 98.7      |

Examples 7 to 8

(S)-4-(3-(4-(2,3-dihydroxypropoxy)phenyl)-4,4-dimethyl-5-carbonyl-2-thioimidazolin-1-yl)-2-(trifluoromethyl)benzonitrile (hereinafter referred to as compound A), lactose, microcrystalline cellulose, croscarmellose sodium or sodium carboxymethyl starch or low substituted hydroxypropyl cellulose were weighed according to the ratio shown in Table 5, then wet granulation was carried out by a high speed shear granulator using an aqueous solution of hydroxypropyl cellulose SSL as a binder. The wet and soft material was wet-milled and dried, then the dry granules (moisture content is less than 3%) were dry-milled. A prescription amount of magnesium stearate was added, and mixed well with the granules. The resulting total mixed granules were compressed into tablets.

TABLE 5

| Components | Examples (mg/tablet) | | |
|---|---|---|---|
|  | 6 | 7 | 8 |
| Compound A | 100.0 | 100 | 100 |
| Lactose | 270.0 | 270.0 | 270.0 |
| Microcrystalline cellulose | 85.0 | 85.0 | 85.0 |
| Croscarmellose sodium | 25.0 | — | — |
| Low substituted hydroxypropyl cellulose | — | — | 25.0 |
| Sodium carboxymethyl starch | — | 25.0 | — |
| Hydroxypropyl cellulose SSL | 10.2 | 10.6 | 13.4 |
| Magnesium stearate | 5.0 | 5.0 | 5.0 |
| Total | 495 | 496 | 498 |

Experimental Example 3: Dissolution Test

The dissolution rates of the tablets of Examples 6-8 were determined according to the second method (paddle method) of the dissolution rate test disclosed in the appendix of volume IV of Chinese Pharmacopeia (2015 Edition). The dissolution test was carried out using 1000 ml of 0.5% aqueous solution of sodium dodecyl sulfate (SDS) as a dissolution medium at 37±0.5° C. and at the paddle speed of 50 rpm. The results show that the dissolution of compound A in Examples 6 and 7 is complete; and the dissolution of compound A in Example 8 is slightly incomplete. The dissolution results are shown in Table 6.

TABLE 6

| Time  | Dissolution rate (%) | | |
|-------|-----------|-----------|-----------|
| (min) | Example 6 | Example 7 | Example 8 |
| 5     | 35.9      | 34.9      | 23.9      |
| 15    | 79.0      | 80.5      | 65.9      |

TABLE 6-continued

| Time | Dissolution rate (%) | | |
|---|---|---|---|
| (min) | Example 6 | Example 7 | Example 8 |
| 30 | 90.1 | 93.2 | 87.5 |
| 45 | 97.9 | 99.8 | 94.2 |
| 60 | 98.0 | 100.2 | 95.9 |

Experimental Example 4: Compatibility Study

When povidones were used as the binder, it was found by the compatibility study of auxiliary materials that the related substances could increase significantly, suggesting that the compatibility between povidones and the drug is poor. However, the stability was good when hydroxypropyl cellulose was used.

TABLE 7

| Items | Study conditions | Study time (weeks) | Appearance | Related substances (%) |
|---|---|---|---|---|
| The drug in combination with polyvinyl-pyrrolidone K30 | Initial point | 0 | Off-white powder | 0.19 |
| | 40° C./RH 75%/open | 2 weeks | Off-white powder | 0.25 |
| | | 4 weeks | Off-white powder | 0.31 |
| | 40° C./RH 75%/closed | 2 weeks | Off-white powder | 0.13 |
| | | 4 weeks | Off-white powder | 0.19 |
| | 60° C./closed | 2 weeks | Off-white powder | 0.47 |
| | | 4 weeks | Pale yellow powder | 0.58 |
| The drug in combination with Hydroxypropyl cellulose SSL | Initial point | 0 | Off-white powder | 0.19 |
| | 40° C./RH 75%/open | 2 weeks | Off-white powder | 0.18 |
| | | 4 weeks | Off-white powder | 0.19 |
| | 40° C./RH 75%/closed | 2 weeks | Off-white powder | 0.19 |
| | | 4 weeks | Off-white powder | 0.19 |
| | 60° C./closed | 2 weeks | Off-white powder | 0.19 |
| | | 4 weeks | Off-white powder | 0.21 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A pharmaceutical composition, comprising (S)-4-(3-(4-(2,3-dihydroxypropoxy)phenyl)-4,4-dimethyl-5-carbonyl-2-thioimidazolin-1-yl)-2-(trifluoromethyl)benzonitrile, and a cellulose ether.

2. The pharmaceutical composition according to claim 1, wherein the cellulose ether is one or more selected from the group consisting of alkyl cellulose, hydroxyalkyl cellulose and hydroxyalkyl alkyl cellulose.

3. The pharmaceutical composition according to claim 2, wherein the hydroxyalkyl cellulose is one or more selected from the group consisting of hydroxyethyl cellulose and hydroxypropyl cellulose.

4. The pharmaceutical composition according to claim 2, wherein the hydroxyalkyl alkyl cellulose is one or more selected from the group consisting of hydroxyethyl methyl cellulose and hydroxypropyl methyl cellulose.

5. The pharmaceutical composition according to claim 1, wherein the cellulose ether is present in an amount of 0.5%-50% by weight, relative to the total weight of the pharmaceutical composition.

6. The pharmaceutical composition according to claim 1, further comprising a filler, wherein the filler comprises one or more selected from the group consisting of lactose, mannitol, microcrystalline cellulose and pregelatinized starch.

7. The pharmaceutical composition according to claim 1, further comprising a disintegrant, wherein the disintegrant comprises one or more selected from the group consisting of croscarmellose sodium, sodium carboxymethyl starch, low-substituted hydroxypropyl cellulose and crospovidone.

8. The pharmaceutical composition according to claim 1, further comprising a lubricant, wherein the lubricant comprises one or more selected from the group consisting of magnesium stearate, stearic acid, and glyceryl behenate.

9. A pharmaceutical composition, comprising:
1) 5%-50% by weight of (S)-4-(3-(4-(2,3-dihydroxypropoxy)phenyl)-4,4-dimethyl-5-carbonyl-2-thioimidazolin-1-yl)-2-(trifluoromethyl)benzonitrile; 2) 0.5%-10% by weight of hydroxypropyl cellulose; 3) 40-80% by weight of a filler, wherein the filler comprises a mixture of lactose and microcrystalline cellulose; 4) 3%-20% by weight of a disintegrant, wherein the disintegrant comprises one or more selected from the group consisting of croscarmellose sodium and sodium carboxymethyl starch; and 5) 0.1-2% by weight of a lubricant, wherein the lubricant comprises one or more selected from the group consisting of magnesium stearate, stearic acid, and glyceryl behenate.

10. A method for preparing a pharmaceutical composition according to claim 1, wherein the method comprises
   a) preparing granules of (S)-4-(3-(4-(2,3-dihydroxypropoxy)phenyl)-4,4-dimethyl-5-carbonyl-2-thioimidazolin-1-yl)-2-(trifluoromethyl)benzonitrile and the cellulose ether by high shear granulation in a mixer, one step granulation in a fluidized bed or direct tableting; and
   b) optionally tableting the granules or filling the granules into a capsule.

11. A method for treating prostate cancer in a subject in need thereof, the method comprising administering to the subject the pharmaceutical composition of claim 1.

12. The pharmaceutical composition according to claim 2, wherein the cellulose ether is hydroxyalkyl cellulose.

13. The pharmaceutical composition according to claim 3, wherein the hydroxyalkyl cellulose is hydroxypropyl cellulose.

14. The pharmaceutical composition according to claim 3, wherein the hydroxyalkyl cellulose is hydroxypropyl cellulose SSL or hydroxypropyl cellulose SL.

15. The pharmaceutical composition according to claim 5, wherein the cellulose ether is present in an amount of 0.5%-15% by weight, relative to the total weight of the pharmaceutical composition.

16. The pharmaceutical composition according to claim 5, wherein the cellulose ether is present in an amount of 0.5%-10% by weight, relative to the total weight of the pharmaceutical composition.

17. The pharmaceutical composition according to claim 6, wherein the filler comprises one or more selected from the group consisting of lactose and microcrystalline cellulose.

18. The pharmaceutical composition according to claim 7, wherein the disintegrant comprises one or more selected from the group consisting of croscarmellose sodium and sodium carboxymethyl starch.

19. A method of treating prostate cancer in a subject in need thereof, the method comprising administering to the subject the pharmaceutical composition of claim 9.

* * * * *